US008574918B2

(12) United States Patent
Hirayama et al.

(10) Patent No.: US 8,574,918 B2
(45) Date of Patent: Nov. 5, 2013

(54) SAMPLE INJECTOR, SAMPLE INJECTING METHOD, AND LIQUID CHROMATOGRAPH

(75) Inventors: Aya Hirayama, Kanagawa (JP); Osamu Shirota, Kanagawa (JP); Masashi Mita, Tokyo (JP); Kazuhiko Mibayashi, Kyoto (JP)

(73) Assignee: Shiseido Company, Ltd., Tokyo (JP)

( * ) Notice: Subject to any disclaimer, the term of this patent is extended or adjusted under 35 U.S.C. 154(b) by 449 days.

(21) Appl. No.: 13/055,720

(22) PCT Filed: Jul. 28, 2009

(86) PCT No.: PCT/JP2009/063400
§ 371 (c)(1),
(2), (4) Date: Jan. 25, 2011

(87) PCT Pub. No.: WO2010/013698
PCT Pub. Date: Feb. 4, 2010

(65) Prior Publication Data
US 2011/0120213 A1    May 26, 2011

(30) Foreign Application Priority Data
Aug. 1, 2008   (JP) ................. 2008-200063

(51) Int. Cl.
*G01N 30/16*   (2006.01)
*G01N 30/18*   (2006.01)
(52) U.S. Cl.
USPC ...... 436/161; 73/61.55; 73/61.56; 210/198.2; 210/656; 422/70
(58) Field of Classification Search
USPC ............... 422/70, 89; 73/61.55, 61.56, 73/23.35–23.42; 210/198.2, 656; 96/101–107; 95/89; 436/161
See application file for complete search history.

(56) References Cited

U.S. PATENT DOCUMENTS

| 2003/0143123 A1 | 7/2003 | Maeda |
| 2008/0134804 A1 | 6/2008 | Maeda et al. |
| 2009/0078031 A1* | 3/2009 | Ono et al. ................... 73/61.55 |
| 2009/0126467 A1 | 5/2009 | Zilioli et al. |

FOREIGN PATENT DOCUMENTS

| EP | 1843153 A1 | 10/2007 |
| GB | 1535441 A | 12/1978 |
| JP | 2003-215118 | 7/2003 |
| JP | 2005-031012 | 2/2005 |
| JP | 2006-201121 | 8/2006 |
| JP | 3 129218 U | 2/2007 |
| JP | 2008-164498 | 7/2008 |
| WO | WO 2008-029422 | 3/2008 |

OTHER PUBLICATIONS

Extended European Search Report mailed Oct. 14, 2011.

* cited by examiner

*Primary Examiner* — Jan Ludlow
(74) *Attorney, Agent, or Firm* — IPUSA, PLLC

(57) ABSTRACT

A sample injection part connected to a column to inject a sample into the column; a sample injection needle attachable to the sample injection part; a sample suction part connectable to the sample injection needle and configured to cause a predetermined amount of the sample to be drawn by suction into the sample injection needle upon connecting to the sample connection needle; a mobile phase supply part configured to supply the column with a mobile phase; a first switching valve for selectively connecting the sample injection needle to one of the sample suction part and the mobile phase supply part; and a second switching valve, including the sample injection part, for supplying the sample and the mobile phase to the column via the sample injection needle in the case of having the sample injection needle attached to the sample injection part and for supplying the mobile phase to the column via the first switching valve in the case of having the sample injection needle removed from the sample injection part are included.

8 Claims, 13 Drawing Sheets

SAMPLE INJECTOR, SAMPLE INJECTING METHOD, AND LIQUID CHROMATOGRAPH

TECHNICAL FIELD

The present invention relates to sample injectors, sample injecting methods, and liquid chromatographs, and particularly to a sample injector, a sample injecting method, and a liquid chromatograph for preventing the occurrence of carryover and improving detection accuracy with a relatively inexpensive configuration.

BACKGROUND ART

Conventionally, liquid chromatographs include a reservoir to store a mobile phase (elution solvent), a pump to supply the mobile phase from the reservoir, a sample injector to inject a sample together with the mobile phase into a tubing leading to a column, the column filled with a packing material for separating components in the sample, an oven to keep the column at a constant temperature, and a detector to detect the separated components in the sample. Of these, the sample injector is so structured as to attach a sample injection needle that has drawn in the sample by suction to a sample injection port (sample injection part) and to inject the sample together with the mobile phase into the tubing via a switching valve.

In recent years, with improvement in the detection sensitivity of liquid chromatographs, a phenomenon called carryover has become a problem. The carryover, which is a phenomenon that an earlier measured sample remains in a liquid chromatograph to present such a detection result as if the substance were present in a currently measured sample, degrades the reliability of analysis results. The carryover is caused by the mixture of a residual sample at the time of injecting the next sample, the residual sample having adhered to a metal and/or a resin inside a sample injector at the time of injecting the sample together with a mobile phase into a tubing and remained.

Therefore, in order to ensure reduction of the carryover, a technique has been proposed that provides two injection needles and attaches a first one of the sample injection needles that has drawn in a sample by suction to a sample injection port, thereby allowing the sample to be supplied to a column without intervention of a switching valve, thus preventing the sample from remaining in the switching valve as it does conventionally and making it possible to sufficiently reduce the carryover. (For example, see Patent Document 1.)

In the apparatus provided with two injection needles illustrated in Patent Document 1, a sample is injected through the process of disconnecting a first sample injection needle in a mobile phase supplying state where the first sample injection needle is connected to an injection part, and connecting a second sample injection needle retaining the sample to the injection and causing a mobile phase to restart flowing into a column.

PRIOR ART DOCUMENT

Patent Document

[Patent Document 1] Japanese Laid-Open Patent Application No. 2006-201121

DISCLOSURE OF THE INVENTION

Problems to Be Solved by the Invention

In the above-described conventional technique, it is possible to prevent the occurrence of carryover, while the two sample injection needles are provided and a complicated control function for controlling them individually may be separately needed. Further, in the sample injection process using the two sample injection needles, a certain period of time is necessary to switch the needles, and the flow of the mobile phase into the column is interrupted during this state change to cause a variation in the pressure inside the column, which is not preferable for stable analysis. Further, a special consideration may be necessary as to a leak of liquid at the time of detaching the two needles.

For the above-described reasons, it is preferable to prevent the occurrence of carryover and improve detection accuracy with a relatively inexpensive configuration in the sample injection process.

Accordingly, the present invention has been made in view of the above-described problems, and has an object of providing a sample injector, a sample injecting method, and a liquid chromatograph for preventing the occurrence of carryover and improving detection accuracy with a relatively inexpensive configuration.

Means for Solving the Problems

In order to solve the above-described problems, the present invention adopts means for solving the problems with the following features.

The present invention is characterized by including a sample injection part connected to a column to inject a sample into the column; a sample injection needle attachable to the sample injection part; a sample suction part connectable to the sample injection needle and configured to cause a predetermined amount of the sample to be drawn by suction into the sample injection needle upon connecting to the sample connection needle; a mobile phase supply part configured to supply the column with a mobile phase; a first switching valve for selectively connecting the sample injection needle to one of the sample suction part and the mobile phase supply part; and a second switching valve, including the sample injection part, for supplying the sample and the mobile phase to the column via the sample injection needle in a case of having the sample injection needle attached to the sample injection part and for supplying the mobile phase to the column via the first switching valve in a case of having the sample injection needle removed from the sample injection part.

This makes it possible to prevent the occurrence of carryover and to improve detection accuracy with a relatively inexpensive configuration.

Further, the second switching valve is characterized by including an insertion and holding member configured to have the sample injection needle inserted thereinto and hold the inserted sample injection needle; and a first path for supplying the sample and the mobile phase to the column, wherein the insertion and holding member is configured to close the first path in a case of having the sample injection needle removed from the insertion and holding member.

This makes it possible to close a path with a simple configuration. This makes it possible to limit the passage of the sample and to prevent carryover.

The present invention is further characterized by including a second path for supplying the mobile phase to the first path in a case of having the first path closed.

This enables continuous supply of the mobile phase to the column. Further, this configuration makes it possible to limit the passage of the sample and to prevent carryover.

Further, the insertion and holding member is characterized by including a moving part for moving an insertion part, into which the sample injection needle is to be inserted, to close the first path, wherein the first switching valve is configured to perform switching so as to prevent a flow of the mobile phase into the column from being interrupted by closing the first path by the moving part.

This makes it possible to ensure closure with a simple mechanism. Further, the switching of the first switching valve, which occurs substantially simultaneously with this closure, allows the mobile phase to flow into the column without a substantial interruption. Further, it is possible to prevent carryover.

Further, the present invention, which is a sample injecting method for injecting a sample into a column using a sample injector including a sample injection part connected to the column to inject the sample into the column; a sample injection needle attachable to the sample injection part; a sample suction part connectable to the sample injection needle and configured to cause a predetermined amount of the sample to be drawn by suction into the sample injection needle upon connecting to the sample connection needle; a mobile phase supply part configured to supply the column with a mobile phase; a first switching valve for selectively connecting the sample injection needle to one of the sample suction part and the mobile phase supply part; and a second switching valve, including the sample injection part, for supplying the sample and the mobile phase to the column via the sample injection needle in a case of having the sample injection needle attached to the sample injection part and for supplying the mobile phase to the column via the first switching valve in a case of having the sample injection needle removed from the sample injection part, is characterized by including a first mobile phase supplying step of connecting the sample injection needle and the mobile phase supply part through path switching performed by the first switching valve and supplying the mobile phase from the sample injection needle to the column in the case of having the sample injection needle attached to the sample injection part; a sample suction step of connecting the sample injection needle and the sample suction part through the path switching performed by the first switching valve and causing the sample to be drawn by suction into the sample injection needle; and a second mobile phase supplying step of supplying the column with the mobile phase from the mobile phase supply part through path switching performed by the first switching valve and the second switching valve while causing the sample to be drawn by suction into the sample injection needle by the sample suction step.

This makes it possible to close a path with a simple configuration. This makes it possible to limit the passage of the sample and to prevent carryover.

The present invention is further characterized by including a closing step of closing a first path for supplying the sample and the mobile phase to the column in a case of having the sample injection needle removed from an insertion part of an insertion and holding member, using the insertion and holding member provided in the second switching valve for having the sample injection needle inserted thereinto and holding the inserted sample injection needle.

This makes it possible to close a path with a simple configuration. This makes it possible to limit the passage of the sample and to prevent carryover.

Further, the second mobile phase supplying step is characterized by supplying the mobile phase to the first path via a second path when the first path is closed.

This enables continuous supply of the mobile phase to the column. Further, this configuration makes it possible to limit the passage of the sample and to prevent carryover.

Further, the closing step is characterized by closing the first path by causing an insertion part provided in the insertion and holding member and configured to have the sample injection needle inserted thereinto to be moved by a moving part, and the second mobile phase supplying step is characterized by causing the first switching valve to perform switching so as to prevent a flow of the mobile phase into the column from being interrupted by closing the first path by the moving part.

This makes it possible to ensure closure with a simple mechanism. Further, the switching of the first switching valve, which occurs substantially simultaneously with this closure, allows the mobile phase to flow into the column without a substantial interruption. Further, it is possible to prevent carryover.

Further, the present invention is a liquid chromatograph characterized by including a sample injector including a sample injection part connected to a column to inject a sample into a column; a sample injection needle attachable to the sample injection part; a sample suction part connectable to the sample injection needle and configured to cause a predetermined amount of the sample to be drawn by suction into the sample injection needle upon connecting to the sample connection needle; a mobile phase supply part configured to supply the column with a mobile phase; a first switching valve for selectively connecting the sample injection needle to one of the sample suction part and the mobile phase supply part; and a second switching valve, including the sample injection part, for supplying the sample and the mobile phase to the column via the sample injection needle in a case of having the sample injection needle attached to the sample injection part and for supplying the mobile phase to the column via the first switching valve in a case of having the sample injection needle removed from the sample injection part.

This makes it possible to provide a liquid chromatograph capable of preventing the occurrence of carryover to be improved in detection accuracy while maintaining a relatively inexpensive configuration.

Effects of the Invention

According to the present invention, it is possible to provide a sample injector, a sample injecting method, and a liquid chromatograph that prevent the occurrence of carryover to be improved in detection accuracy with a relatively inexpensive configuration.

DESCRIPTION OF EMBODIMENT

A description is given below, using drawings, of an embodiment in which a sample injector, a sample injecting method, and a liquid chromatograph are suitably implemented.

[General Configuration of Liquid Chromatograph]

Figure 1:
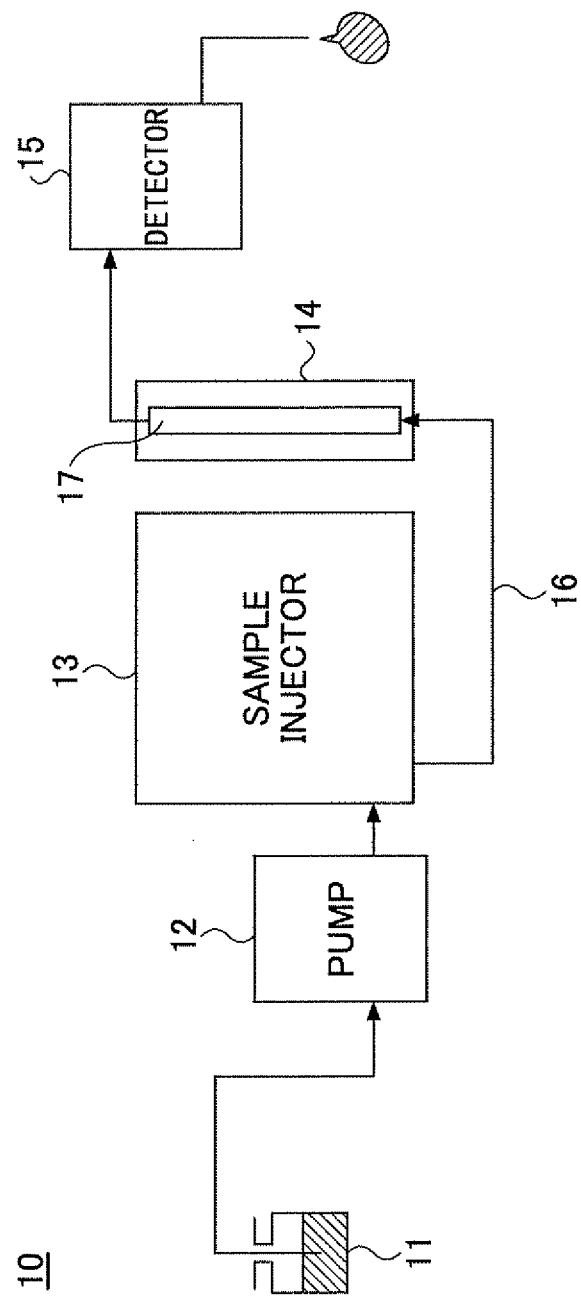
FIG. 1 is a block diagram illustrating a liquid chromatograph in an embodiment.

First, a description is given, using a drawing, of a general configuration of a liquid chromatograph having a sample injector in the present invention. FIG. 1 is a diagram illustrating a general configuration of a liquid chromatograph in this embodiment.

A liquid chromatograph 10 illustrated in FIG. 1 is configured to have a reservoir (eluent bath) 11, a pump (mobile phase supply part) 12, a sample injector 13, a column oven 14, and a detector 15.

The reservoir 11 stores a mobile phase (elution solvent) that is an eluent. The pump 12 continuously flows the mobile phase stored in the reservoir 11 into the sample injector 13.

The sample injector 13 injects a sample and the mobile phase into a tubing 16 to the column oven 14, etc. A description is given below of a specific apparatus configuration of the sample injector 13 and a specific sample injecting method, etc., in the present invention.

The column oven 14 keeps at a constant temperature a separation column 17 filled with a packing material for separating components in the sample injected from the tubing 16. The detector 15 detects separated components (chemical substances and so on). In order to stabilize measurement, it is preferable that the mobile phase be constantly supplied from the reservoir 11 to the column 17 via the sample injector 13 by the pump 12.

In the present invention, the liquid chromatograph is not limited in configuration to the above-described one, and, for example, a degasser to degas the mobile phase may be provided between the reservoir (eluent bath) 11 and the pump 12.

[Sample Injector 13: Functional Configuration]

Figure 2:
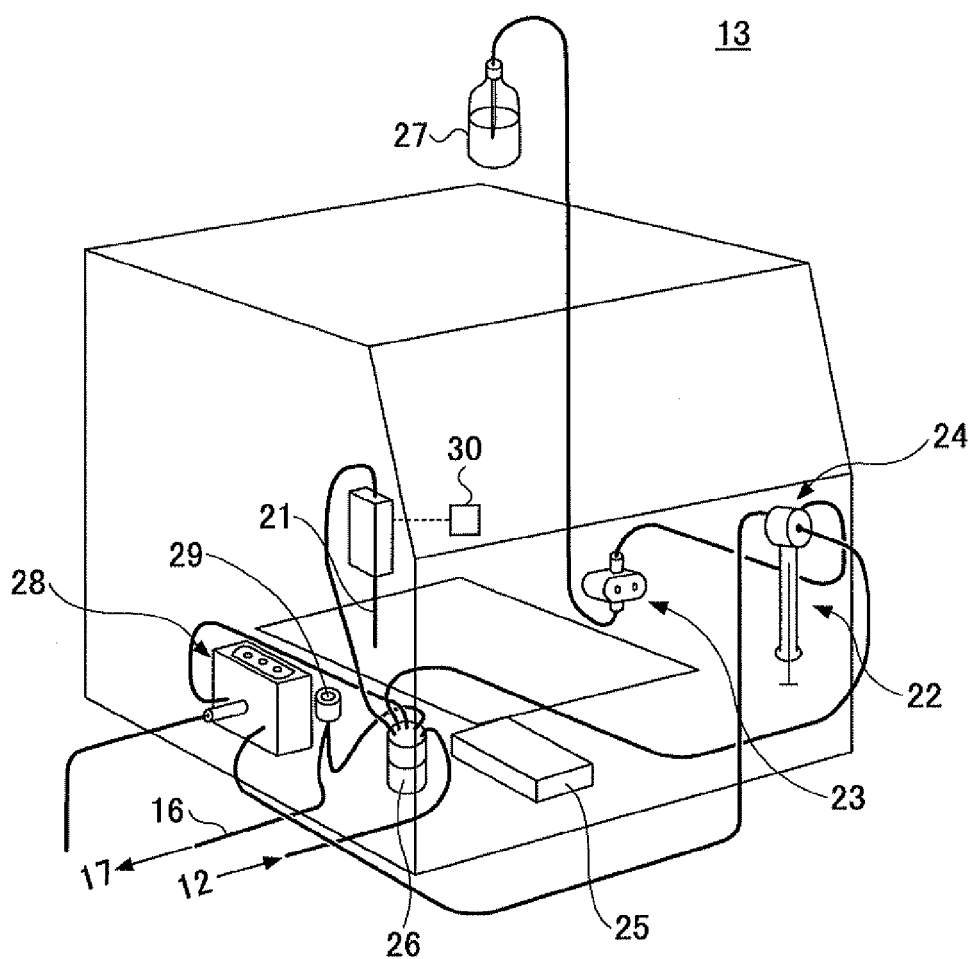
FIG. 2 is a perspective view illustrating a sample injector in this embodiment.

Next, a description is given, using a drawing, of a functional configuration of the sample injector 13 applied to the liquid chromatograph 10 as described above, etc. FIG. 2 is a diagram illustrating a functional configuration of a sample injector in this embodiment. The sample injector 13 illustrated in FIG. 2 is configured to have a sample injection needle 21, a syringe (sample suction part) 22, a wash liquid pump 23, a valve 24, a sample container 25, an injection valve (first switching valve) 26, a wash liquid container 27, a cleaner 28, a direct injection valve (second switching valve) 29, and a needle moving part 30.

The sample injection needle 21 is connectable to the syringe 22 via the injection valve 26 and the valve 24. Further, the sample injection needle 21 is also connectable to the wash liquid pump 23 via the injection valve 26.

Here, upon connection of the sample injection needle 21 to the syringe 22 through path switching performed by the valve 24, a sample may be drawn into by suction and discharged from the sample injection needle 21 by the pulling and pushing of the syringe 22.

Upon connection of the sample injection needle 21 to the wash liquid pump 23 via the injection valve 26 through path switching performed by the injection valve 26, wash liquid (for example, water or the like) inside the wash liquid container 27 is supplied to the sample injection needle 21.

The valve 24 causes wash liquid delivered from the wash liquid container 27 by the wash liquid pump 23 to be supplied selectively to the cleaner 28 or the sample injection needle 21. Specifically, the valve 24 has, for example, three ports P1 through P3, and can selectively connect two of them.

Here, the syringe 22 and the injection valve 26 are connected to a single port (for example, P3) of the valve 24, so that the syringe 22 and the injection valve 26 are constantly connected. The valve 24 is also allowed to make the ports P1 through P3 unconnected to one another.

The sample container 25 has a sample stored inside. A predetermined necessary amount of the sample stored in the sample container 25 is drawn in by suction by the sample injection needle 21, and is discharged to a sample injection part (direction injection port) provided in the direct injection valve 29.

The injection valve 26 is, for example, configured to have six ports (for example, a high-pressure six-way valve). Further, the injection valve 26 has the pump 12, the sample injection needle 21, the valve 24, the cleaner 28, and the direction injection valve 29 connected to five of the six ports. Further, the injection valve 26 is configured to switch multiple preset connections as required.

The wash liquid container 27 has wash liquid stored inside and is connected to the wash liquid pump 23. The wash liquid stored in the wash liquid container 27 has a predetermined amount necessary for cleaning drawn in by suction by the wash liquid pump 23 to be pumped to the valve 24.

The cleaner 28 is, for example, configured to include a cleaning part, an ultrasonic vibrator, a waste liquid port, and a waste liquid tubing. Further, upon connection to the wash liquid pump 23 through path switching performed by the valve 24, the cleaner 28 is supplied with wash liquid from the wash liquid container 27. A surplus of the wash liquid over a predetermined amount flows into the waste liquid port to be discharged outside as waste liquid from the waste liquid tubing connected to the waste liquid port.

Further, upon insertion of the sample injection needle 21 into the cleaner 28, the cleaner 28 cleans the sample injection needle 21 of an adhered sample. The cleaner 28 has the function of preventing the occurrence of carryover by this. Further, the cleaner 28, which is provided with an ultrasonic vibrator, is configured to allow ultrasonic cleaning of the sample injection needle 21. This makes it possible to improve a cleaning effect on the sample injection needle 21 and to further ensure prevention of the occurrence of carryover.

The direct injection valve 29, which is a feature of the present invention, is a mechanism for injecting a sample and a mobile phase into the column 17 provided in the column oven 14. The direct injection valve 29 is provided with a sample injection part (direct injection port). The sample injection part is connected to the separation column 17. That is, in the sample injector 13 in this embodiment, the sample injection part is completely separate from and independent of the injection valve 26. Accordingly, as a result of the sample injection needle 21 that has drawn in a sample by suction being attached to the sample injection part and discharging the sample to the sample injection part, this sample is delivered to the column 17 with a flow of a mobile phase without going through the injection valve 26.

Further, the direct injection valve 29 has the mechanism of delivering only a mobile phase to the column 17 by switching paths when the sample injection needle 21 has been detached by the needle moving part 30 and is performing another operation, such as when taking in a sample. A description is given below of a specific mechanism of the direct injection valve 29.

The needle moving part 30 moves the sample injection needle 21 to a predetermined position at a predetermined time based on a preset sample injection procedure or the like.

As described above, by providing the direct injection valve 29, it is possible to prevent carryover, which is conventionally caused by the passage of a sample through the injection valve 26, with a relatively inexpensive configuration, and to improve detection accuracy.

[Structure of Direct Injection Valve 29]

Figure 3A:
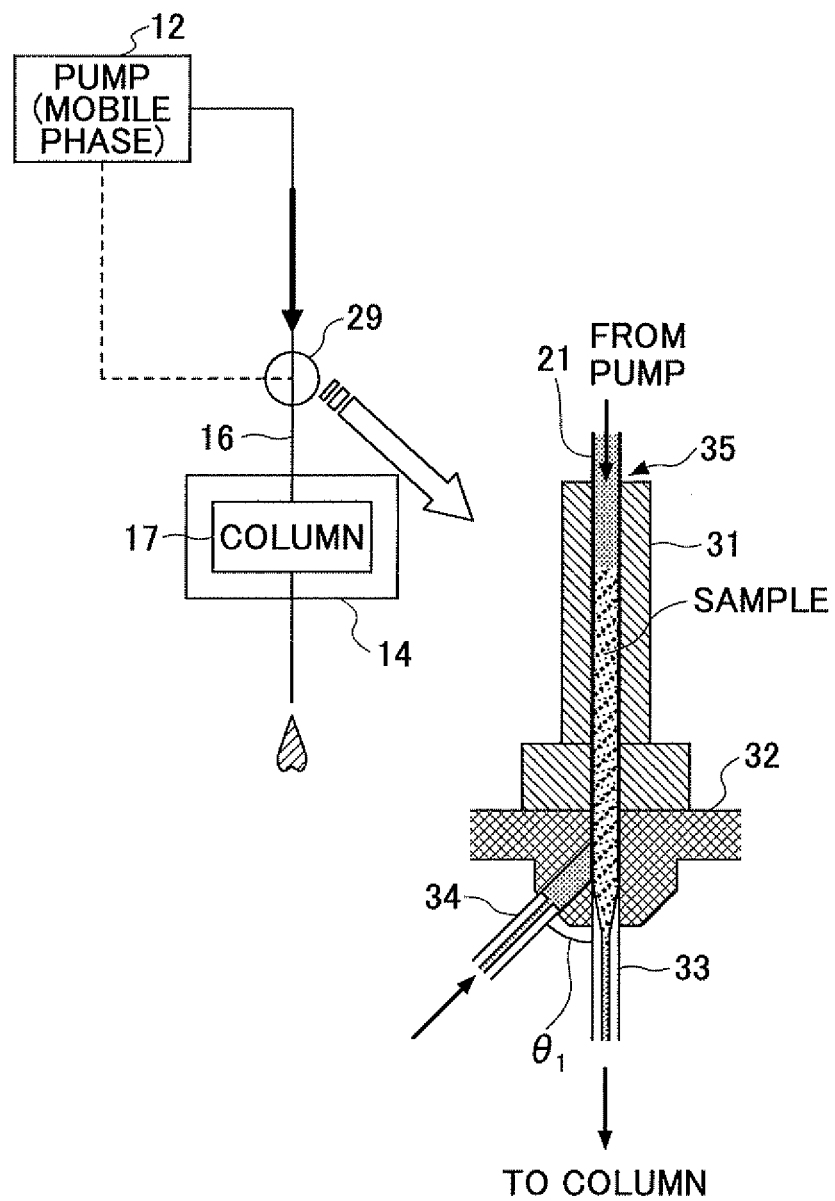
FIG. 3A is a (first) diagram for illustrating a specific example of a direct injection valve.
Figure 3B:
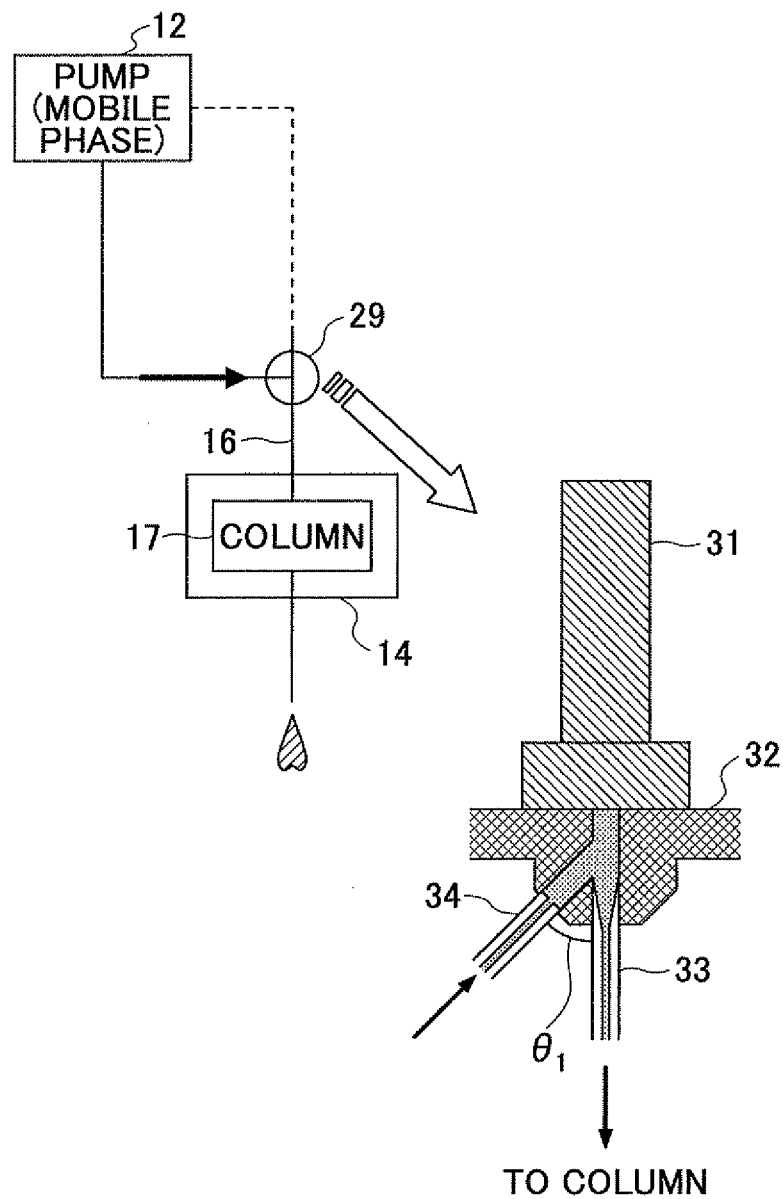
FIG. 3B is a (second) diagram for illustrating the specific example of the direction injection valve.

Here, a description is given, using drawings, of a specific example of the above-described direct injection valve 29. FIG. 3A and FIG. 3B are diagrams for illustrating a specific example of the direct injection valve. FIG. 3A and FIG. 3B illustrate states where the paths are switched from each other. That is, in this embodiment, the direct injection valve 29 switches to the connection of FIG. 3A or FIG. 3B.

The direct injection valve 29 illustrated in FIG. 3A and FIG. 3B is configured to have an insertion and holding member 31 where the sample injection needle 21 is to be inserted and held; a base 32; a first path 33 foamed of a tubing directly connected to the column 17, etc., the first path 33 being failed in the base 32 in order to cause a sample and a mobile phase to be injected into the column 17 inside the column oven 14; and a second path 34 formed of a tubing, etc., the second path 34 continuing to inject the mobile phase to the first path 33 from a side at a predetermined angle $\theta_1$ and having the mobile phase flowing in to prevent the flow of the mobile phase into the column 17 from being interrupted. As illustrated in FIG. 3A and FIG. 3B, the first path 33 is tapered in correspondence to the end shape of the sample injection needle 21 in order to facilitate its joining with the sample injection needle 21.

Here, for the above-described insertion and holding member 31, PEEK (polyether ether ketone), metal such as stainless steel or titanium, etc., may be used. Further, the above-described predetermined angle $\theta_1$ may be determined to be any angle based on the positions and the sizes of the first path 33 and the second path 34 in the device configuration. In the present invention, the predetermined angle $\theta_1$ is not limited in particular, but is preferably, for example, such an angle as to cause no stagnation in the flow of the mobile phase supplied from the second path 34 to the first path 33.

As illustrated in FIG. 3A, in the case where the sample injection needle 21 is inserted through an insertion part 35 of the insertion and holding member 31 up to a position partway through the first path 33, the mobile phase from the pump 12 is flown into the first path 33 via the sample injection needle 21 to be delivered to the column 17. Further, the sample is also injected from the sample injection needle 21.

Further, as illustrated in FIG. 3B, with the sample injection needle 21 removed from the insertion and holding member 31, the position of the insertion part 35 for the sample injection needle 21 provided in the insertion and holding member 31 is moved by rotation or sliding to close one end of the first path 33.

The mobile phase from the pump 12 is flown into the first path 33 through the second path 34 in order to prevent the closure of the one end of the first path 33 from stopping the supply of the mobile phase to the column 17. This makes it possible to maintain the flow of the first path 33 and to continuously supply the column 17 with the mobile phase.

For the direct injection valve 29, in place of one with multiple paths among ports such as the above-described injection valve 26, a path switching valve such as a three-way valve may be used.

Figure 4A:
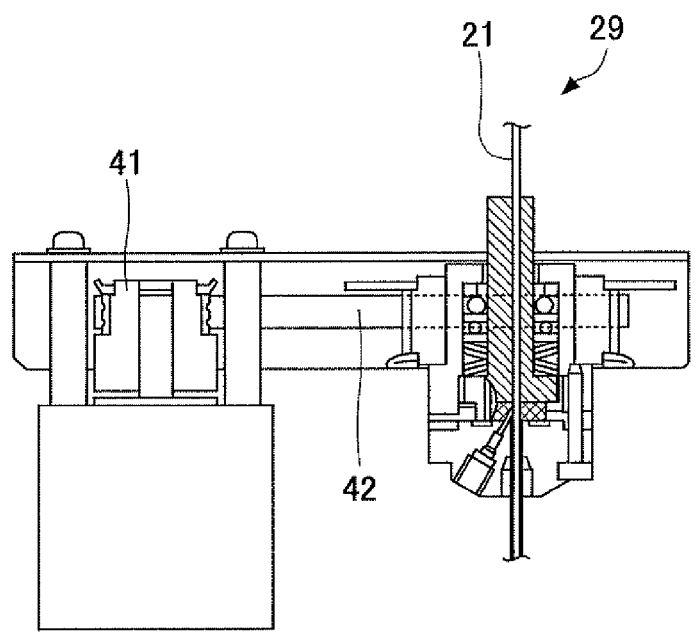
FIG. 4A is a (first) diagram illustrating a device configuration of the direct injection valve.
Figure 4B:
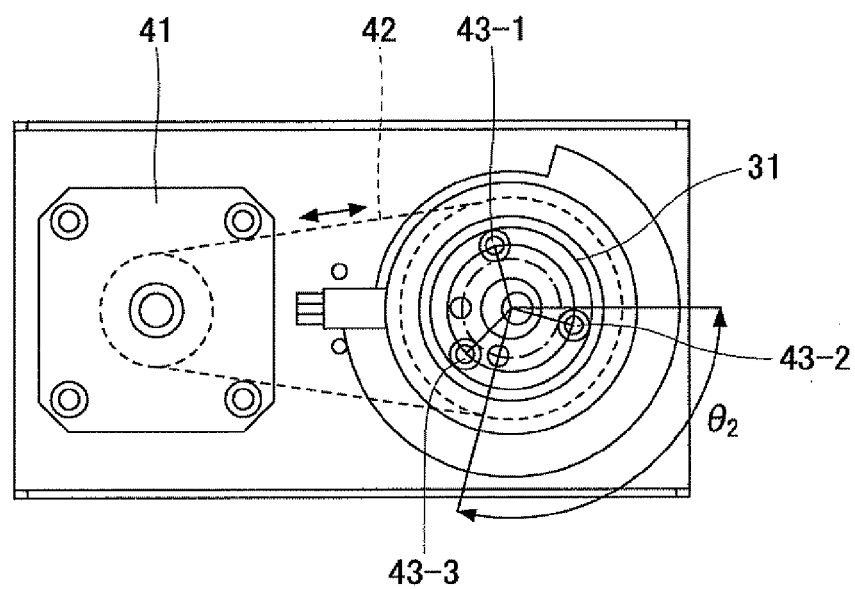
FIG. 4B is a (second) diagram illustrating the device configuration of the direct injection valve.
Figure 4C:
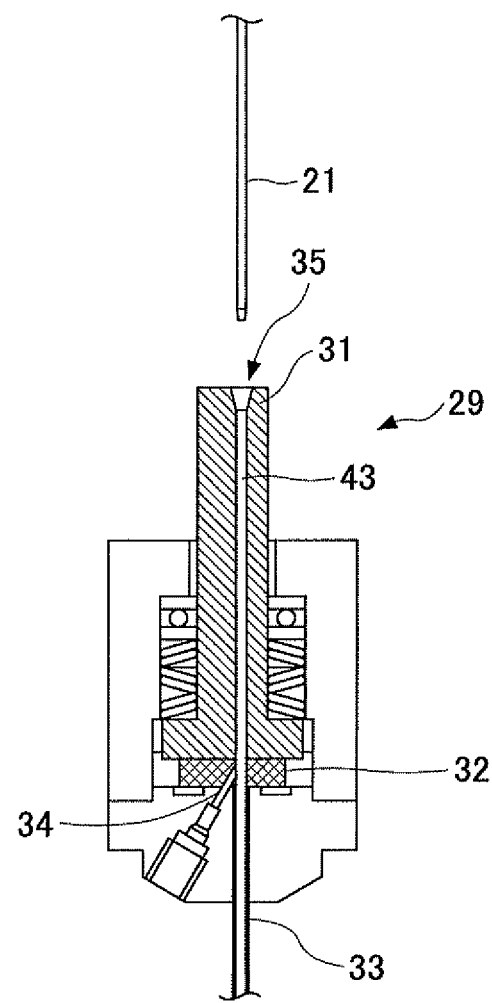
FIG. 4C is a (third) diagram illustrating the device configuration of the direct injection valve.

Here, FIG. 4A through FIG. 4C are diagrams illustrating a device configuration of the direct injection valve 29. FIG. 4A illustrates the direct injection valve 29 and a drive part (moving part) 41 for causing the direct injection valve 29 to operate. FIG. 4B is a bottom side view of FIG. 4A. FIG. 4C is a diagram illustrating the sample injection needle 21 detached from the insertion and holding member 31.

In the case illustrated in FIG. 4A through FIG. 4C, the drive part 41 for rotating the insertion and holding member 31 of the direct injection valve 29 is provided. For example, a motor or the like may be used for the drive part 41. Further, the insertion and holding member 31 of the direct injection valve 29 may be rotated by, for example, up to a predetermined angle $\theta_2$ about an axis by providing the insertion and holding member 31 of the direct injection valve 29 with a turning force from the drive part through a belt member 42.

Thereby, when the sample injection needle 21 is pulled out as illustrated in FIG. 4C, it is possible to make a needle insertion path 43, provided at a position offset from the axis of rotation of the insertion and holding member 31, and the first path 33 unconnected and to close the one end of the first path 33 with the bottom surface of the insertion and holding member 31 by moving the insertion and holding member 31 by the predetermined angle $\theta_2$ in a predetermined direction with the belt member 42 as illustrated in FIG. 4B. This results in the above-described state as illustrated in FIG. 3B. Further, in the case of inserting the sample injection needle 21, it is possible to supply the column 17 with the sample and the mobile phase by causing the drive part 41 to rotate the insertion and holding member 31 through the belt member 42 to connect the needle insertion path 43 and the first path 33 and further inserting the sample injection needle 21 as illustrated in FIG. 3A described above.

In this embodiment, the insertion and holding member 31 may have multiple needle insertion paths (three needle insertion paths 43-1 through 43-3 in the case of FIG. 4B). In the case where multiple needle insertion paths are provided, any of the paths and the first path 33 may be connected. This makes it possible to further improve detection accuracy by using different needle insertion paths 43 depending on the kind of the sample, etc.

Further, in the above-described embodiment illustrated in FIG. 4A through FIG. 4C, a case is illustrated where the needle insertion path 43 is moved by the rotation of the insertion and holding member 31, caused by the drive part 41 using the belt member 42, so as to close one end of the first path 33. However, the present invention is not limited to this, and the one end of the first path 33 may be closed by, for example, moving the needle insertion path 43 by causing the insertion and holding member 31 to slide by a moving part.

[Sample Injecting Method Using Sample Injector 13]

Next, a specific description is given, with reference to FIG. 5 through FIG. 10, of a sample injecting method using the sample injector 13 in this embodiment. FIG. 5 through FIG. 10, which illustrate operating states of a sample injection procedure used in this embodiment, illustrate states at a standby time (during analysis), at a sample taking time, at a time of preliminary cleaning of the sample injection needle, at a time of ultrasonic cleaning of the sample injection needle, at a sample injecting time, and at a time of replacing ultrasonic cleaning port wash liquid (during analysis), respectively.

Figure 5:
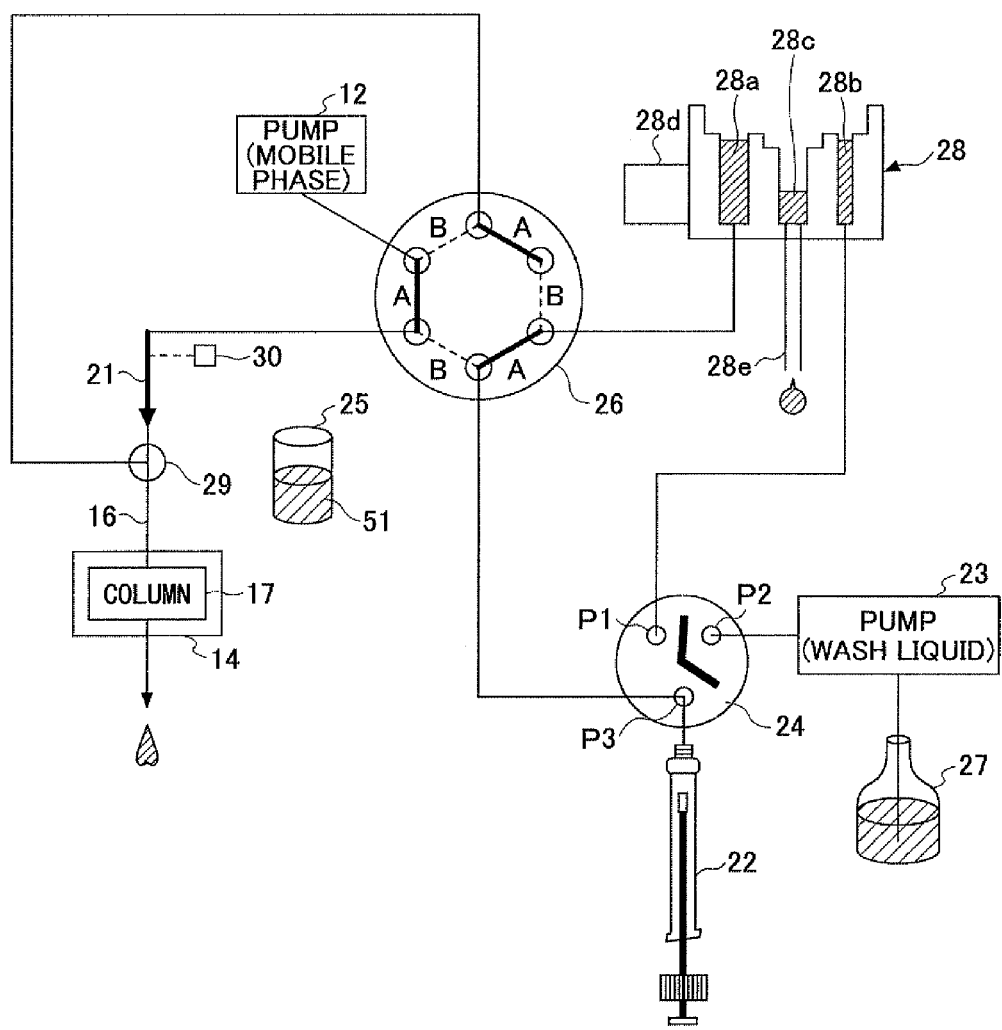
FIG. 5 is a diagram illustrating the state of the sample injector at a standby time (or during analysis) in this embodiment.
Figure 6:
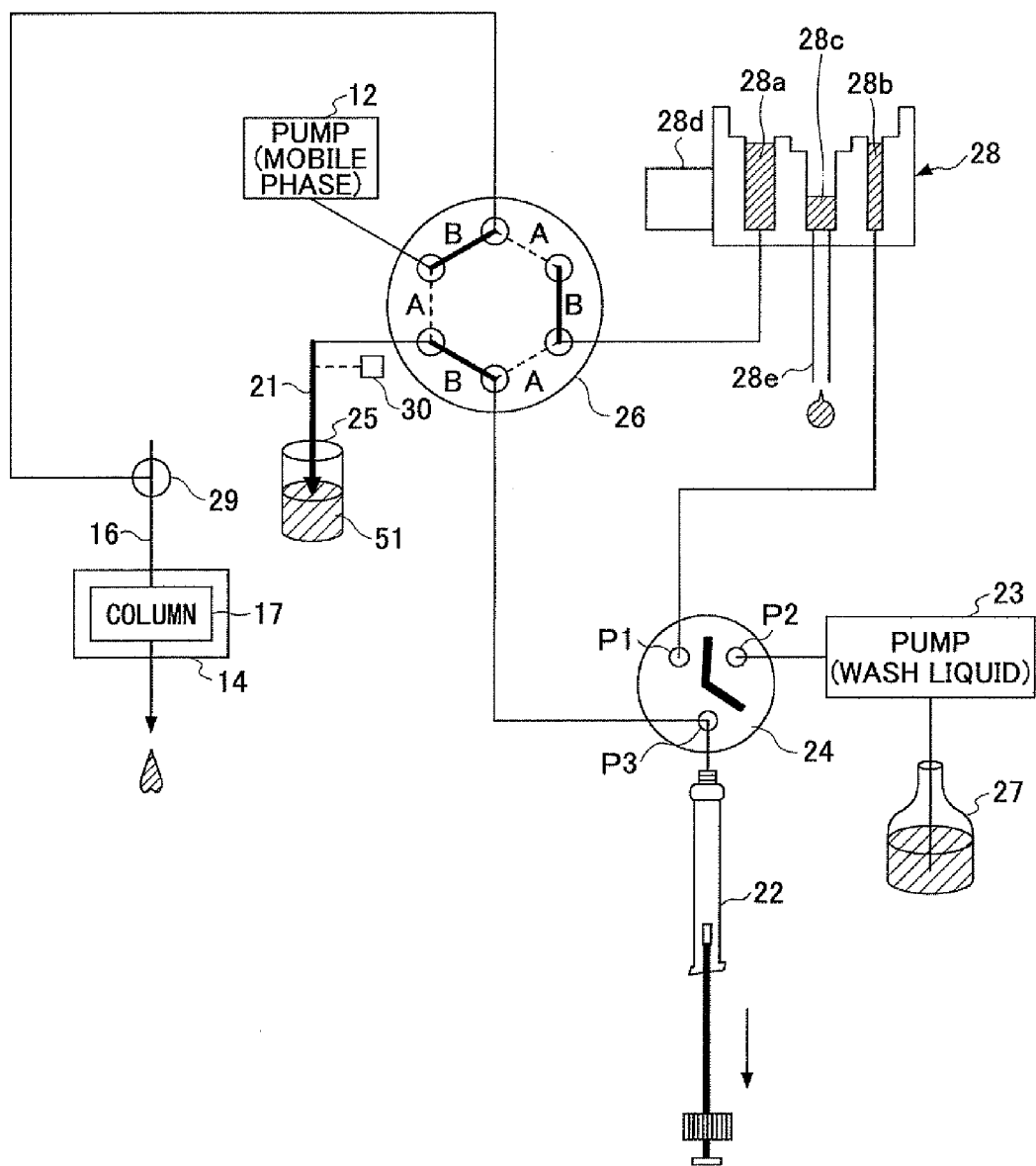
FIG. 6 is a diagram illustrating the state of the sample injector at a sample taking time in this embodiment.
Figure 7:
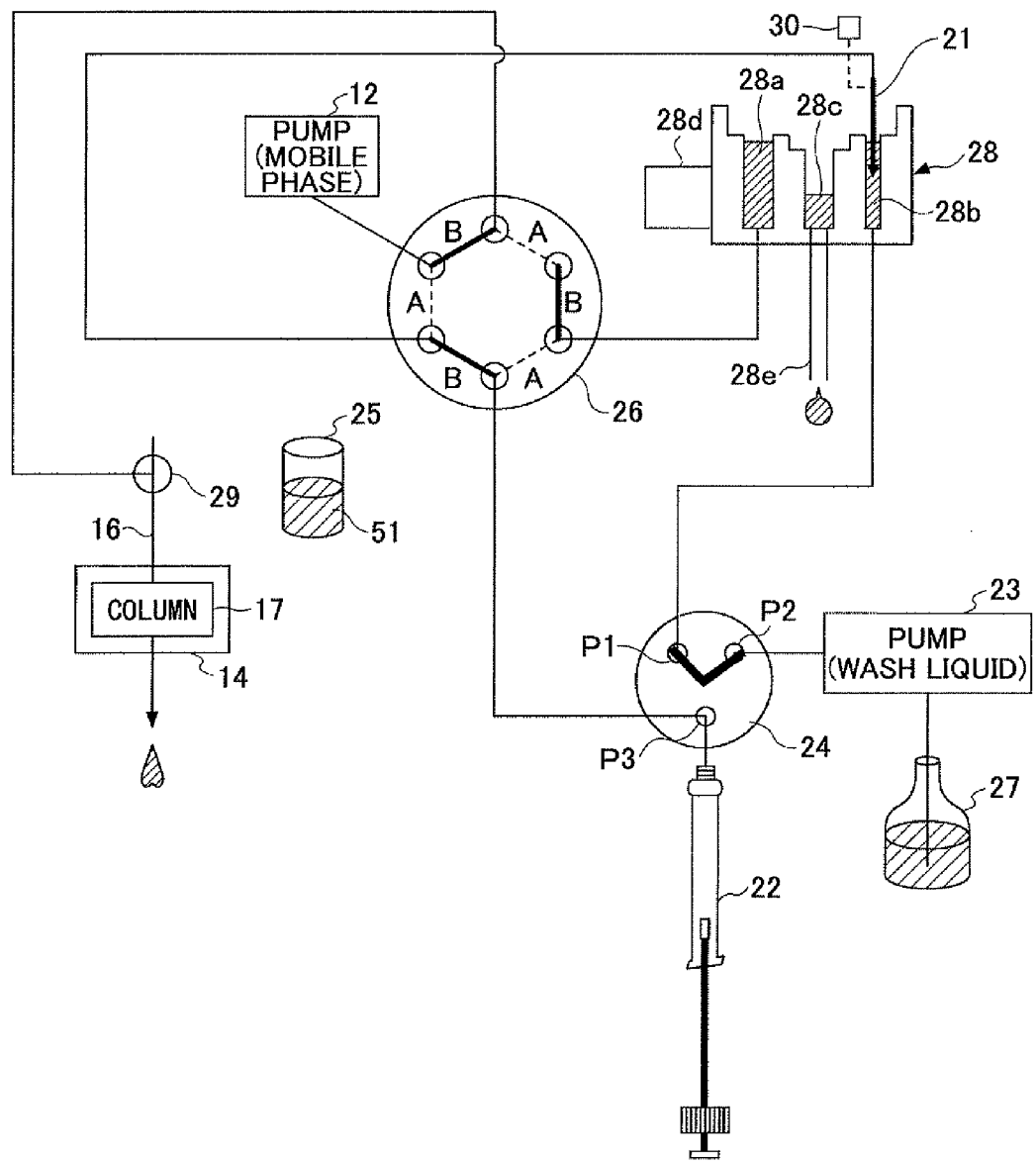
FIG. 7 is a diagram illustrating the state of the sample injector at the time of preliminary cleaning of the sample injection needle in this embodiment.
Figure 8:
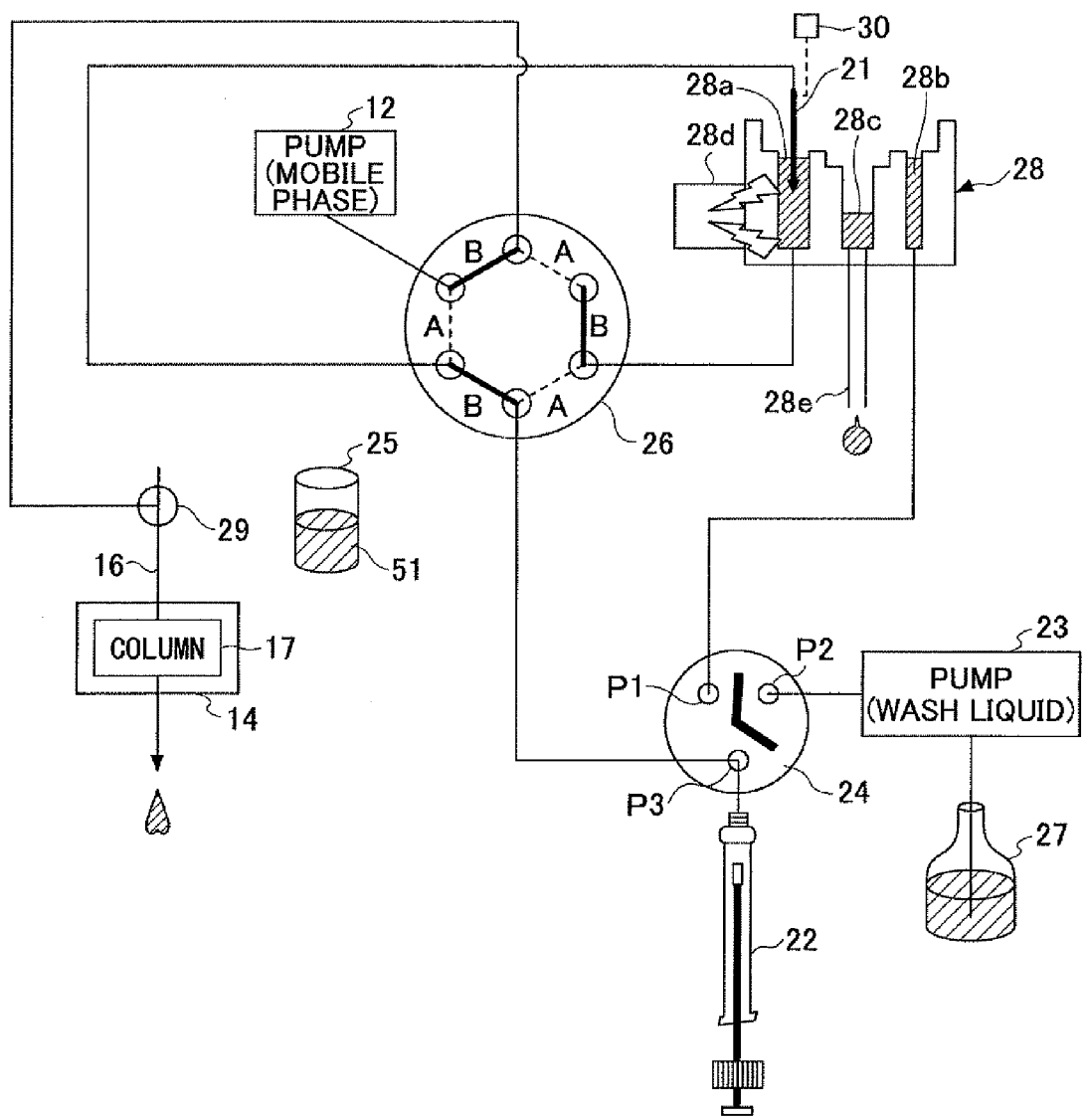
FIG. 8 is a diagram illustrating the state of the sample injector at the time of ultrasonic cleaning of the sample injection needle in this embodiment.
Figure 9:
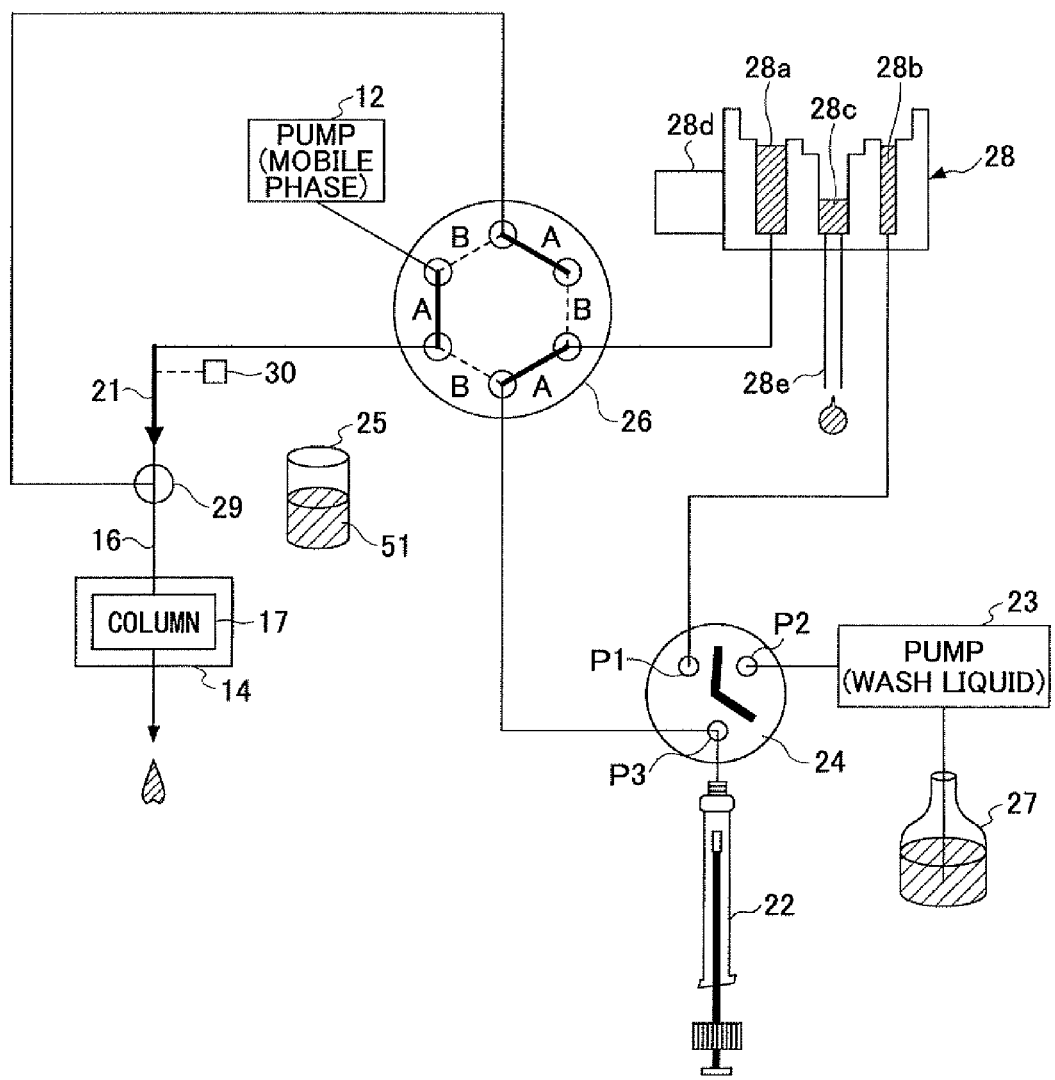
FIG. 9 is a diagram illustrating the state of the sample injector at a sample injecting time in this embodiment.
Figure 10:
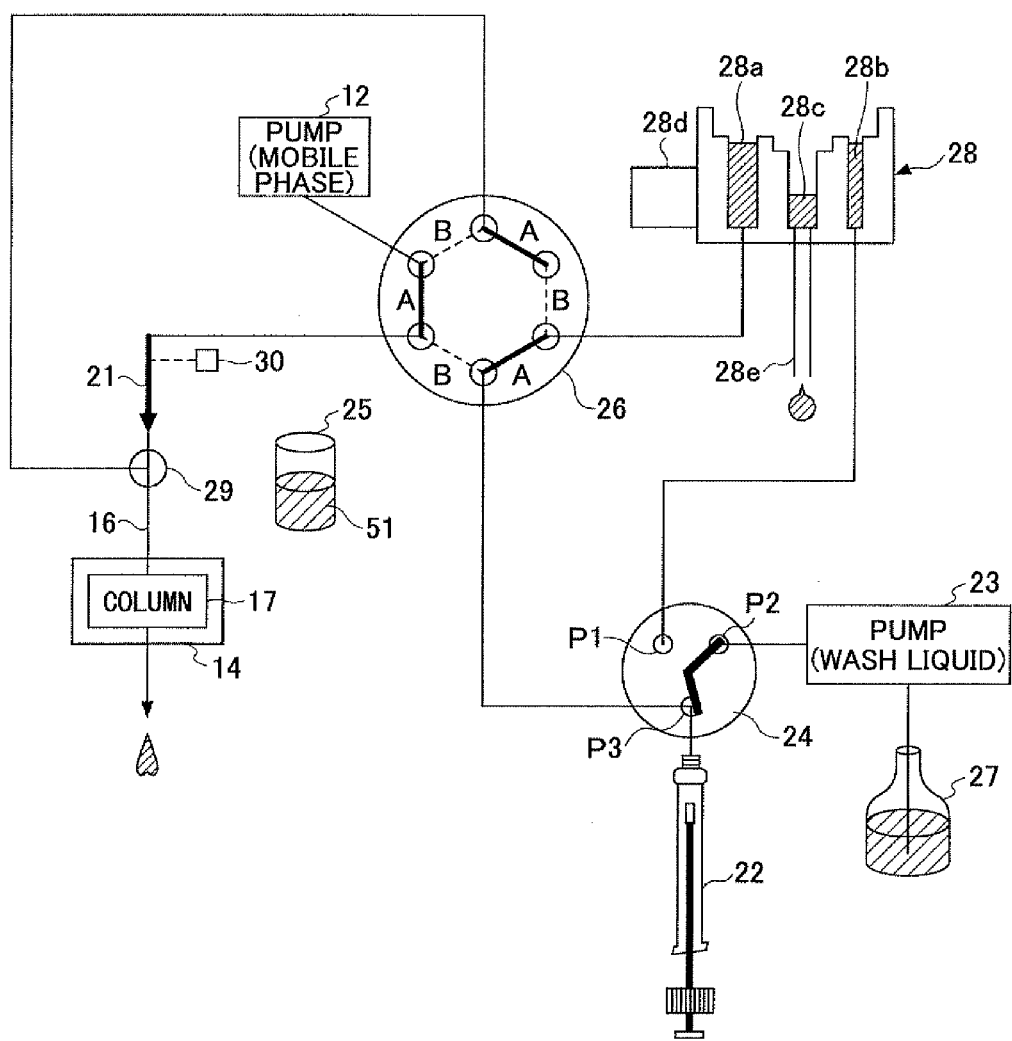
FIG. 10 is a diagram illustrating the state of the sample injector at the time of replacing ultrasonic cleaning port wash liquid (or during analysis) in this embodiment.

To be specific, FIG. 5 is a diagram illustrating the state of the sample injector at a standby time (or during analysis) in this embodiment. FIG. 6 is a diagram illustrating the state of the sample injector at a sample taking time in this embodiment. FIG. 7 is a diagram illustrating the state of the sample injector at the time of preliminary cleaning of the sample injection needle in this embodiment. FIG. 8 is a diagram illustrating the state of the sample injector at the time of ultrasonic cleaning of the sample injection needle in this embodiment. Further, FIG. 9 is a diagram illustrating the state of the sample injector at a sample injecting time in this embodiment. Further, FIG. 10 is a diagram illustrating the state of the sample injector at the time of replacing ultrasonic cleaning port wash liquid (or during analysis) in this embodiment.

In the configuration illustrated in FIG. 5 through FIG. 10, the injection valve 26 is provided with six ports, of which five are connected to the pump 12, the sample injection needle 21, the valve 24, the cleaner 28, and the direct injection valve 29. Further, the valve 24 and the injection valve 26 may switch a connection indicated by A in the drawings (hereinafter referred to as Connection State A) and a connection indicated by B in the drawings (hereinafter referred to as Connection State B). A path indicated by solid line illustrates an actual connection, and a path indicated by broken line illustrates a connection that is not established.

For example, when the injection valve 26 is in Connection State A, the sample injection needle 21 is connected to the pump 12 via the injection valve 26, and the valve 24 is connected to a cleaning part 28a of the cleaner 28 via the injection valve 26. Further, when the injection valve 26 is in Connection State B, the sample injection needle 21 is connected to the valve 24 via the injection valve 26, and the pump 12 is connected to the direct injection valve 29 via the injection valve 26.

That is, the sample injection needle 21 is caused to connect to the syringe 22 through path switching performed by the valve 24 and the injection valve 26, and a sample (sample vial) 51 in the sample container 25 is drawn into by suction and discharged from the sample injection needle 21 by the pulling and pushing of the syringe 22. Further, upon connection of the sample injection needle 21 to the pump 12 through path switching performed by the injection valve 26, a mobile phase is supplied from the pump 12 to the sample injection needle 21.

The valve 24 may selectively supply the cleaner 28 or the sample injection needle 21 with wash liquid pumped by the wash liquid pump 23. Specifically, the valve 24 has the three ports P1 through P3 and may selectively connect two of them. The valve 24 may also establish no connections among the ports P1 through P3.

Further, each of the syringe 22 and the injection valve 26 is connected to the port P3 of the valve 24. That is, the syringe 22 and the injection valve 26 are constantly connected.

Further, the cleaner 28 is configured to have the cleaning part 28a, a cleaning part 28b, a waste liquid port 28c, an ultrasonic vibrator 28d, and a waste liquid tubing 28e. Upon connection to the wash liquid pump 23 through the switching of the valve 24, the cleaner 28 is supplied with wash liquid from the wash liquid container 27. Further, a surplus of the wash liquid over a predetermined amount flows into the waste liquid port 28c to be discharged outside as waste liquid from the waste liquid tubing 28e connected to the waste liquid port 28c. Further, as described below, by inserting the sample injection needle 21 into the cleaner 28, the exterior wall of the sample injection needle 21 to which the sample 51 adheres is cleaned. This makes it possible to prevent the occurrence of carryover.

Further, the cleaner 28 is provided with the ultrasonic vibrator 28d and may perform ultrasonic cleaning on the sample injection needle 21. This makes it possible to improve a cleaning effect on the sample injection needle 21 and to further ensure prevention of the occurrence of carryover.

The tubing 16 connects the direct injection valve 29 and the column 17 inside the column oven 14. That is, the tubing 16 is not connected to the injection valve 26, and is separate from and independent of the injection valve 26. Accordingly, as described below, the sample injection needle 21 that has drawn in the sample 51 in the sample container 25 by suction is attached to the sample injection part of the direct injection valve 29 of the tubing 16 to discharge the sample 51 to the sample injection part, so that the sample 51 flows through the tubing 16 together with a mobile phase to be supplied to the column 17.

Next, a specific description is given of a sample injecting method using the sample injector of the present invention. First, as illustrated in FIG. 5, in a standby state before taking in the sample 51 (or during analysis), the injection valve 26 is in Connection State A, and the valve 24 establishes no connections among the ports P1 through P3. Further, the sample injection needle 21 is moved by the needle moving part 30 and attached to the sample injection part of the direct injection valve 29. Accordingly, at the standby state, the mobile phase supplied from the pump 12 is supplied to the column 17 via the sample injection needle 21 and the direct injection valve 29.

Next, as illustrated in FIG. 6, at the time of taking in the sample 51 in the sample injection needle 21, the sample injection needle 21 is inserted into the sample container 25 by the needle moving part 30. Further, the injection valve 26 is switched to Connection State B, so that the sample injection needle 21 is connected to the syringe 22 and the pump 12 is connected to the direct injection valve 29. Accordingly, at the sample taking time, the mobile phase supplied from the pump 12 is supplied to the column 17 via the injection valve 26 and the direct injection valve 29. Accordingly, the mobile phase is constantly supplied to the column 17, so that it is possible to stabilize measurement.

Further, the sample injection needle 21 is connected to the syringe 22 via the injection valve 26 and the valve 24. Therefore, by performing suction using the syringe 22, a predetermined amount of the sample 51 in the sample container 25 is drawn into the sample injection needle 21. At this point, the amount of suction of the sample 51 is so determined as to not allow the drawn sample to enter the injection valve 26. This makes it possible to prevent the sample 51 from adhering to the inside of the injection valve 26 and to prevent the occurrence of carryover. In order to increase the amount of suction of the sample 51, a sample loop for storing a sample may be provided in the sample injection needle 21.

Next, when the sample taking is completed, the sample injection needle 21 to which the sample 51 has adhered is cleaned because the sample 51 adheres to the exterior wall of the sample injection needle 21. Specifically, the sample injection needle 21 is subjected to preliminary cleaning and ultrasonic cleaning.

As illustrated in FIG. 7, at the time of subjecting the sample injection needle 21 to preliminary cleaning, the sample injection needle 21 is inserted into the cleaning part 28b of the cleaner 28 with the needle moving part 30 while keeping the injection valve 26 in Connection State B. Further, the valve 24 is switched so as to connect the ports P1 and P2, and wash liquid in the wash liquid container 27 is supplied to the cleaning part 28b via the wash liquid pump 23. Accordingly, the wash liquid spouts out into the cleaning part 28b, so that the exterior wall of the sample injection needle 21 is preliminarily cleaned. Wash liquid that has overflowed from the cleaning part 28b is discharged via the waste liquid port 28c and the waste liquid tubing 28e.

As illustrated in FIG. 8, at the time of subjecting the sample injection needle 21 to ultrasonic cleaning, the sample injection needle 21 is inserted into the cleaning part 28a of the cleaner 28 with the needle moving part 30 while keeping the injection valve 26 in Connection State B. Further, the valve 24 is again switched to the state of no connections among the ports P1 through P3. In this state, the ultrasonic vibrator 28d is driven to generate ultrasonic waves, thereby causing ultrasonic vibrations in the wash liquid with which the cleaning part 28a is loaded so that the exterior wall of the sample injection needle 21 is ultrasonically cleaned.

At the time of preliminary cleaning and at the time of ultrasonic cleaning as well, the mobile phase is supplied from the pump 12 to the tubing 16 to the column 17 via the injection valve 26 and the direct injection valve 29.

Next, when the ultrasonic cleaning is completed, the sample 51 that has been taken in the sample injection needle 21 is supplied to the column 17 to analyze the sample 51.

As illustrated in FIG. 9, at the time of analyzing the sample 51, the injection valve 26 switches again to Connection State A from Connection State B, and the sample injection needle 21 is moved to be attached to the sample injection part of the direct injection valve 29 by the needle moving part 30. Further, the sample injection needle 21 that has drawn in the sample 51 by suction is connected to the pump 12 through the injection valve 26. As a result, the sample 51 inside the sample injection needle 21 is supplied to the column 17 without passing through the injection valve 26. Further, the sample 51 supplied to the column 17 is subjected to predetermined separation in the column 17 and is thereafter sent to the detector 15 and analyzed.

At the time of sample analysis, the wash liquid of the cleaning part 28a of the cleaner 28 may be replaced. In this case, as illustrated in FIG. 10, the valve 24 is switched so as to connect the ports P2 and P3 of the valve 24, and the wash liquid in the wash liquid container 27 is supplied to the cleaning part 28a via the valve 24 and the injection valve 26 using the wash liquid pump 23. As a result, the wash liquid contaminated by cleaning the sample injection needle 21 is discharged via the waste liquid port 28c and the waste liquid tubing 28e, and the cleaning part 28a is supplied with uncontaminated wash liquid. This makes it possible to clean the exterior wall of the sample injection needle 21 with more reliability at the next ultrasonic cleaning time

[Example Detection Results in Detector 15]

Next, a description is given, using a drawing, of detection results obtained by analysis with the detector 15 using a sample obtained by the above-described sample injecting method in this embodiment.

Figure 11:
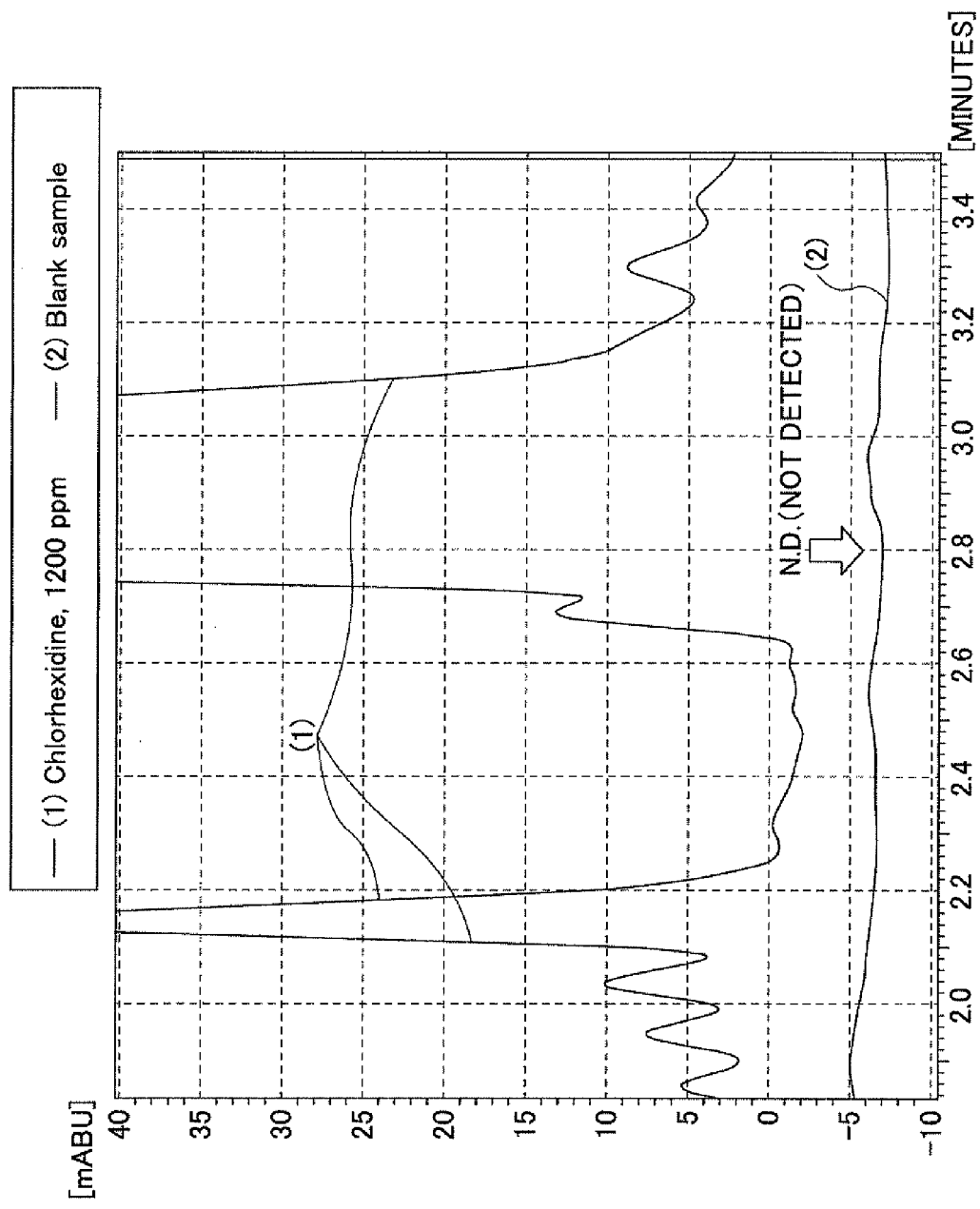
FIG. 11 is a graph illustrating detection results in a detector.

FIG. 11 is a graph illustrating detection results in the detector 15. The graph illustrated in FIG. 11, which is the results of detection of chlorhexidine carryover under a gradient condition using the above-described configuration of the sample injector 13, shows time (MINUTES) on the horizontal axis and absorbance (mABU, milli-absorbance unit) on the vertical axis.

Further, as analysis conditions, CAPCELL PAK IF manufactured by Shiseido Co., Ltd., 2.0 mm in inner diameter and 50 mm in length, was used for the column; (A) 100 mM $NaClO_4$, 10 mM $NH_4H_2PO_4$ (pH 2.6) and (B) acetonitrile were used for the mobile phase; the gradient condition B % was 30% (0 min)→70% (3.0 min)→70% (3.5 min)→30% (3.6 min); the column oven temperature was 25° C.; the object of detection was UV 260 nm; the samples were (1) chlorhexidine 1200 ppm and (2) a blank sample; and the amount of injection was 2 μL each. The results of measuring (2) immediately after (1) are illustrated.

According to this embodiment, as illustrated in FIG. 11, even when a blank sample presenting data values as (2) was injected immediately after the injection of a dense sample presenting data values as (1), nothing was eluted and no carryover was detected because sample (1) did not remain in the system at all.

That is, as illustrated in FIG. 11, according to the configuration of this embodiment, it is possible to prevent the occurrence of carryover and to improve detection accuracy because of the absence of contamination although the system (gradient condition) is severe where a residual sample, however little it may be in amount, is condensed by the gradient to make carryover easier to observe.

As described above, according to the present invention, it is possible to provide a sample injector, a sample injecting method, and a liquid chromatograph for preventing the occurrence of carryover and improving detection accuracy with a relatively inexpensive configuration.

A description is given above of a preferred embodiment of the present invention. The present invention, however, is not limited to this particular embodiment, and variations and modifications may be made within the scope of the gist of the present invention described in Claims.

The present international application claims priority based on Japanese Patent Application No. 2008-200063, filed on Aug. 1, 2008, the entire contents of which are incorporated herein by reference.

DESCRIPTION OF THE REFERENCE NUMERALS 10 liquid chromatograph
11 reservoir (eluent bath)
12 pump
13 sample injector
14 column oven
15 detector
16 tubing
17 column
21 sample injection needle
22 syringe
23 wash liquid pump
24 valve
25 sample container
26 injection valve
27 wash liquid container
28 cleaner
29 direct injection valve
30 needle moving part
31 insertion and holding member
32 base
33 first path
34 second path
41 drive part
42 belt member
43 needle insertion path
51 sample

The invention claimed is:

1. A sample injector, comprising:
   a sample injection part connected to a column to inject a sample into the column;
   a sample injection needle attachable to the sample injection part;
   a sample suction part connectable to the sample injection needle and configured to cause a predetermined amount of the sample to be drawn by suction into the sample injection needle upon connecting to the sample connection needle;
   a mobile phase supply part configured to supply the column with a mobile phase;
   a first switching valve for selectively connecting the sample injection needle to one of the sample suction part and the mobile phase supply part; and
   a second switching valve, including the sample injection part, for supplying the sample and the mobile phase to the column via the sample injection needle in a case of having the sample injection needle attached to the sample injection part and for supplying the mobile phase to the column via the first switching valve in a case of having the sample injection needle removed from the sample injection part,
   the second switching valve including
       a first path for supplying the sample and the mobile phase to the column; and
       a second path for supplying the mobile phase to the first path in the case of having the sample injection needle removed from the sample injection part,
   wherein the second path is configured to be closed by the sample injection needle inserted through the sample injection part into the first path in the case of having the sample injection needle attached to the sample injection part.

2. The sample injector as claimed in claim 1, wherein the second switching valve comprises:
   an insertion and holding member configured to have the sample injection needle inserted thereinto and hold the inserted sample injection needle,
   wherein the insertion and holding member is configured to close the first path in a case of having the sample injection needle removed from the insertion and holding member.

3. The sample injector as claimed in claim 2, wherein the insertion and holding member comprises:
   a moving part for moving an insertion part, into which the sample injection needle is to be inserted, to close the first path,
   wherein the first switching valve is configured to perform switching so as to prevent a flow of the mobile phase into the column from being interrupted by closing the first path by the moving part.

4. A sample injecting method for injecting a sample into a column using a sample injector including a sample injection part connected to the column to inject the sample into a column; a sample injection needle attachable to the sample injection part; a sample suction part connectable to the sample injection needle and configured to cause a predetermined amount of the sample to be drawn by suction into the sample injection needle upon connecting to the sample connection needle; a mobile phase supply part configured to supply the column with a mobile phase; a first switching valve for selectively connecting the sample injection needle to one of the sample suction part and the mobile phase supply part; and a second switching valve, including the sample injection part, for supplying the sample and the mobile phase to the column via the sample injection needle in a case of having the sample injection needle attached to the sample injection part and for supplying the mobile phase to the column via the first switching valve in a case of having the sample injection needle removed from the sample injection part, the sample injecting method comprising:
   a first mobile phase supplying step of connecting the sample injection needle and the mobile phase supply part through path switching performed by the first switching valve and supplying the mobile phase from the sample injection needle to the column in the case of having the sample injection needle attached to the sample injection part;
   a sample suction step of connecting the sample injection needle and the sample suction part through the path switching performed by the first switching valve and causing the sample to be drawn by suction into the sample injection needle; and
   a second mobile phase supplying step of supplying the column with the mobile phase from the mobile phase supply part through path switching performed by the first switching valve and the second switching valve while causing the sample to be drawn by suction into the sample injection needle by the sample suction step,
   wherein the second switching valve includes a first path for supplying the sample and the mobile phase to the column and a second path for supplying the mobile phase to the first path in the case of having the sample injection needle removed from the sample injection part, and
   the second path is closed by the sample injection needle inserted through the sample injection part into the first path in the case of having the sample injection needle attached to the sample injection part.

5. The sample injecting method as claimed in claim 4, further comprising:
   a closing step of closing the first path in a case of having the sample injection needle removed from an insertion part of an insertion and holding member, using the insertion and holding member provided in the second switching valve for having the sample injection needle inserted thereinto and holding the inserted sample injection needle.

6. The sample injecting method as claimed in claim 5, wherein the second mobile phase supplying step supplies the mobile phase to the first path via the second path when the first path is closed.

7. The sample injecting method as claimed in claim 5, wherein:
   the closing step closes the first path by causing the insertion part of the insertion and holding member configured to have the sample injection needle inserted thereinto to be moved by a moving part, and
   the second mobile phase supplying step causes the first switching valve to perform switching so as to prevent a flow of the mobile phase into the column from being interrupted by closing the first path by the moving part.

8. A liquid chromatograph, comprising:
   a sample injector,
   the sample injector including a sample injection part connected to a column to inject a sample into the column; a sample injection needle attachable to the sample injection part; a sample suction part connectable to the sample injection needle and configured to cause a predetermined amount of the sample to be drawn by suction into the sample injection needle upon connecting to the sample connection needle; a mobile phase supply part configured to supply the column with a mobile phase; a first switching valve for selectively connecting the sample injection needle to one of the sample suction part and the mobile phase supply part; and a second switching valve, including the sample injection part, for supplying the sample and the mobile phase to the column via the sample injection needle in a case of having the sample injection needle attached to the sample injection part and for supplying the mobile phase to the column via the first switching valve in a case of having the sample injection needle removed from the sample injection part, the second switching valve including
- a first path for supplying the sample and the mobile phase to the column; and
- a second path for supplying the mobile phase to the first path in the case of having the sample injection needle removed from the sample injection part, wherein the second path is configured to be closed by the sample injection needle inserted through the sample injection part into the first path in the case of having the sample injection needle attached to the sample injection part.

* * * * *